United States Patent [19]

Winner

[11] Patent Number: 4,464,653
[45] Date of Patent: Aug. 7, 1984

[54] COMBUSTIBLE GAS DETECTION SYSTEM

[75] Inventor: Joe K. Winner, Pinellas, Fla.

[73] Assignee: The Bendix Corporation, Southfield, Mich.

[21] Appl. No.: 328,779

[22] Filed: Dec. 9, 1981

[51] Int. Cl.³ .................. G08B 23/00; G08C 19/16
[52] U.S. Cl. .......................... 340/501; 340/870.04; 340/870.16; 340/870.18; 340/870.21; 340/632; 73/23; 324/464; 422/94; 422/98
[58] Field of Search ........... 340/501, 500, 539, 870.21, 340/870.07, 870.04, 870.05, 870.09, 870.12, 870.13, 870.16, 870.17, 870.18, 632–634; 73/23, 26; 116/67 R; 324/464, 465; 422/80, 83, 93, 50, 94, 96, 98

[56] References Cited
U.S. PATENT DOCUMENTS 3,852,730 12/1974 Commins .................. 340/870.21
3,964,018 6/1976 Strait et al. ................ 340/870.09
4,231,249 11/1980 Zuckerman ................ 340/632
4,311,895 1/1982 Tanabe .................... 340/634
4,328,494 5/1982 Goodall .................... 340/870.04

Primary Examiner—Donnie L. Crosland
Attorney, Agent, or Firm—Bruce L. Lamb; W. G. Christoforo

[57] ABSTRACT

A combustible gas detection system in which remotely located combustible gas sensors of the analog type are monitored by a central controller. The sensor analog data is converted to digital data and transmitted to the controller. The controller tests the integrity and validity of data received from the sensor, identifies the nature of any faults therein and vocally signals the cause of such faults. The controller computes the concentration of combustible gas at the sensor and automatically determines sensor calibration constants from received sensor data.

7 Claims, 14 Drawing Figures

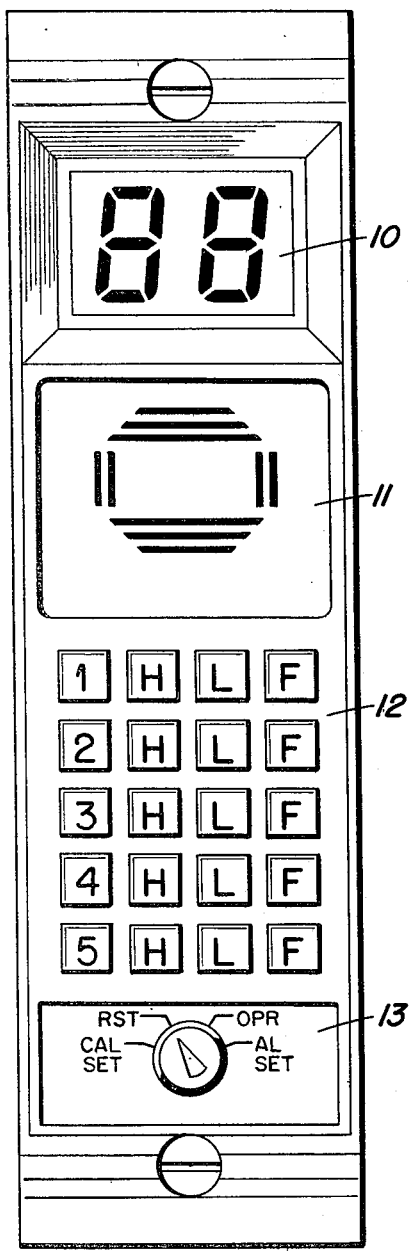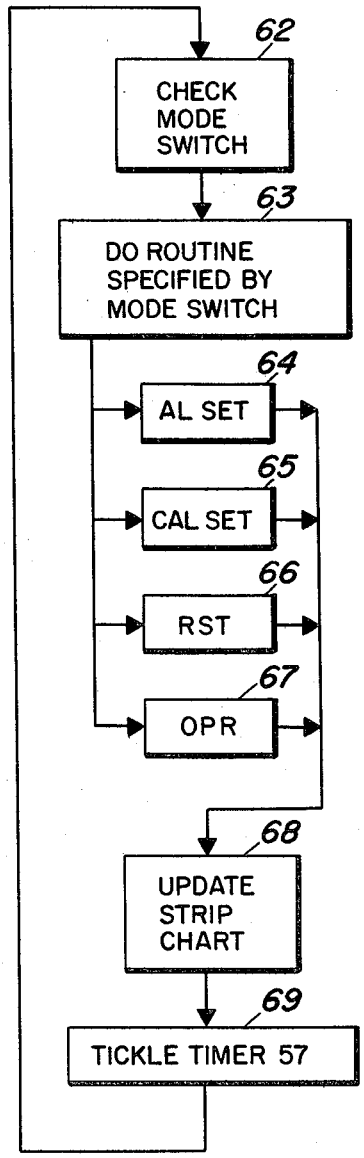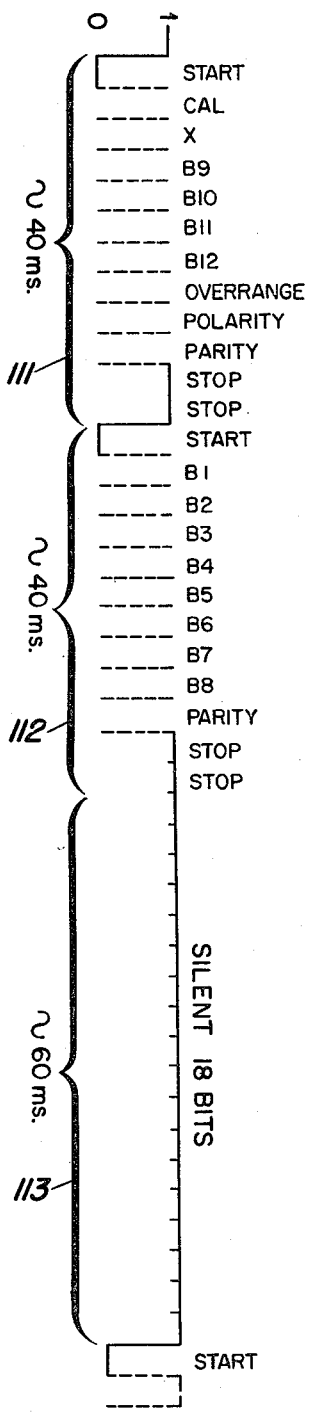

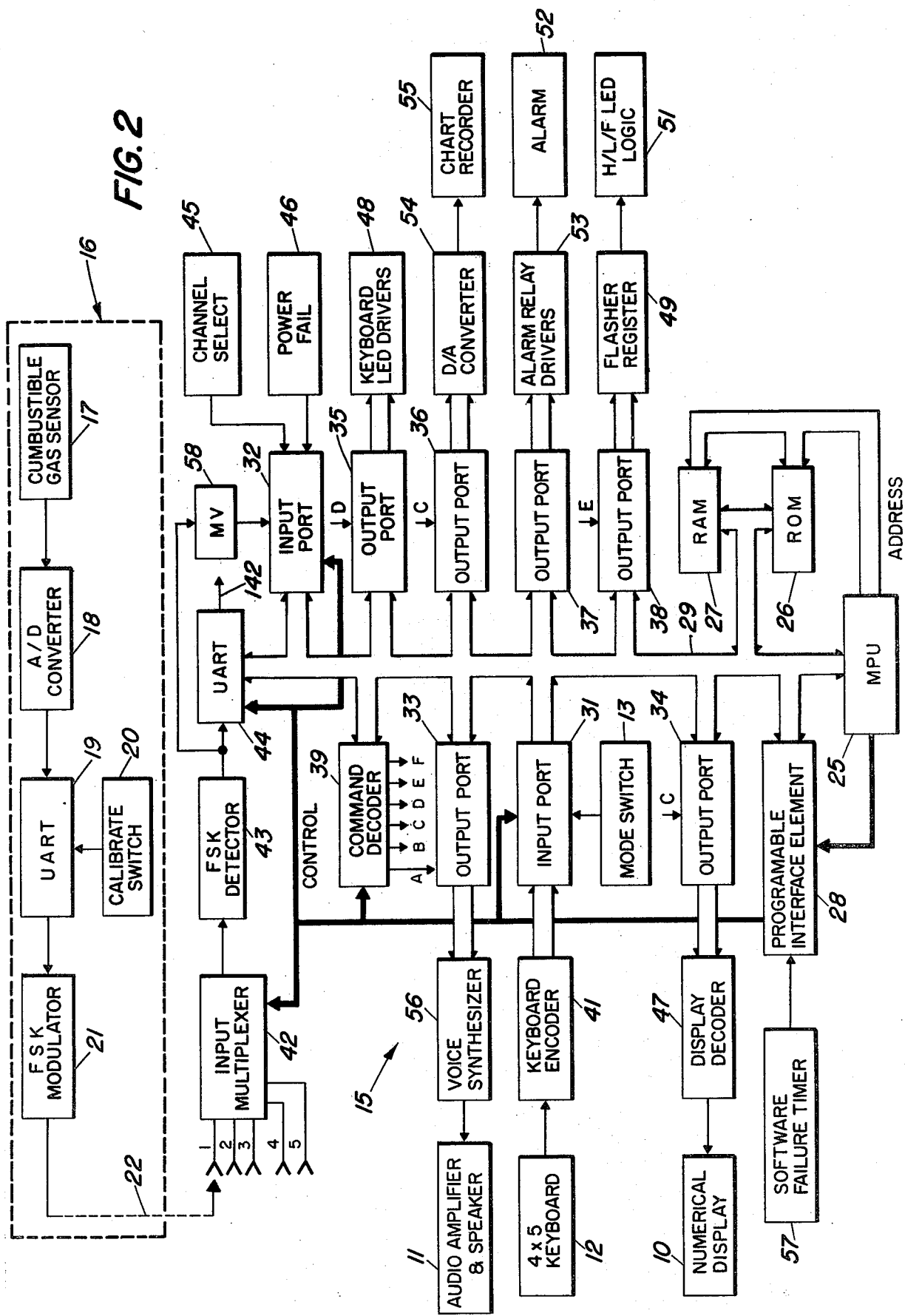

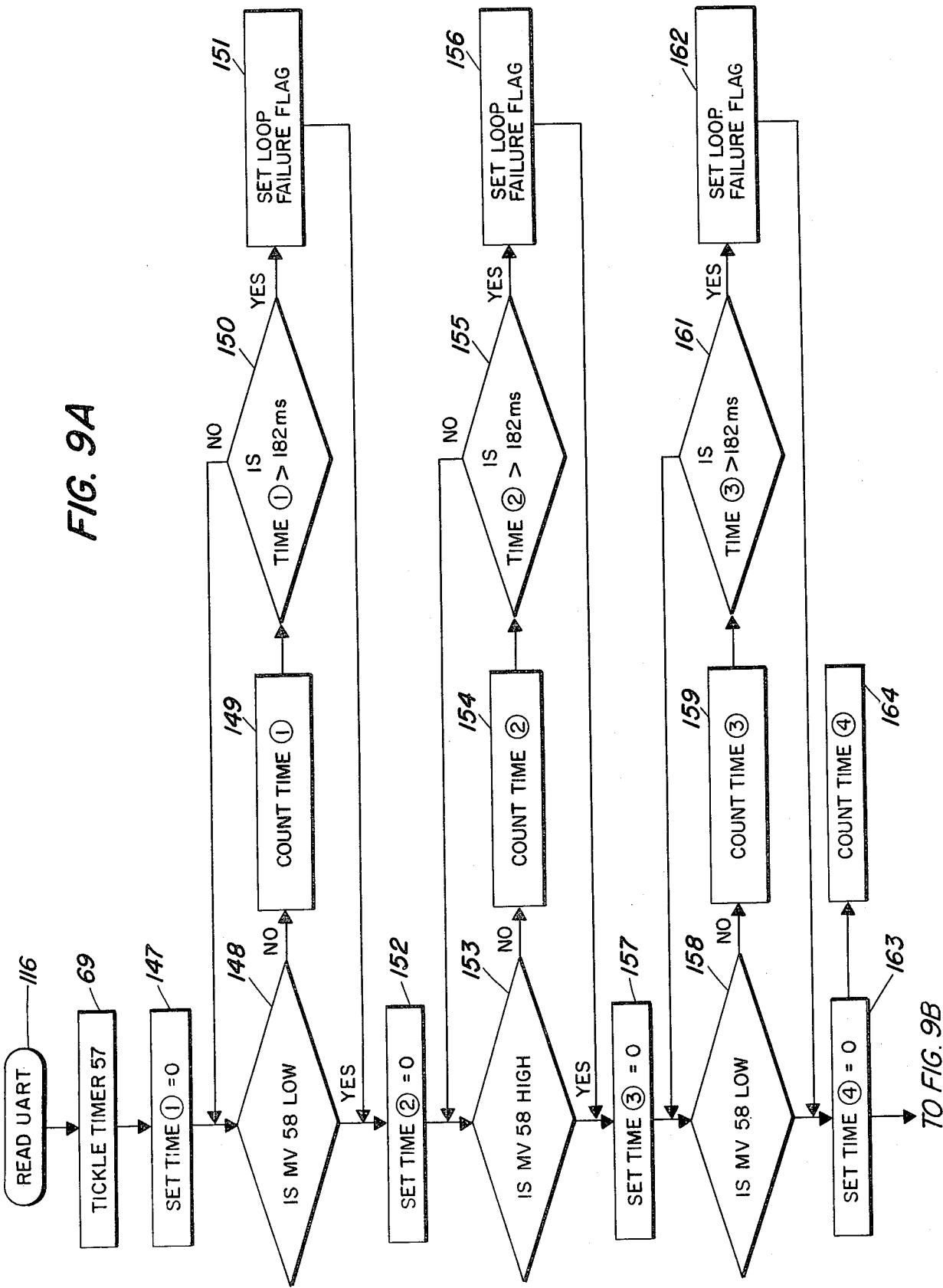

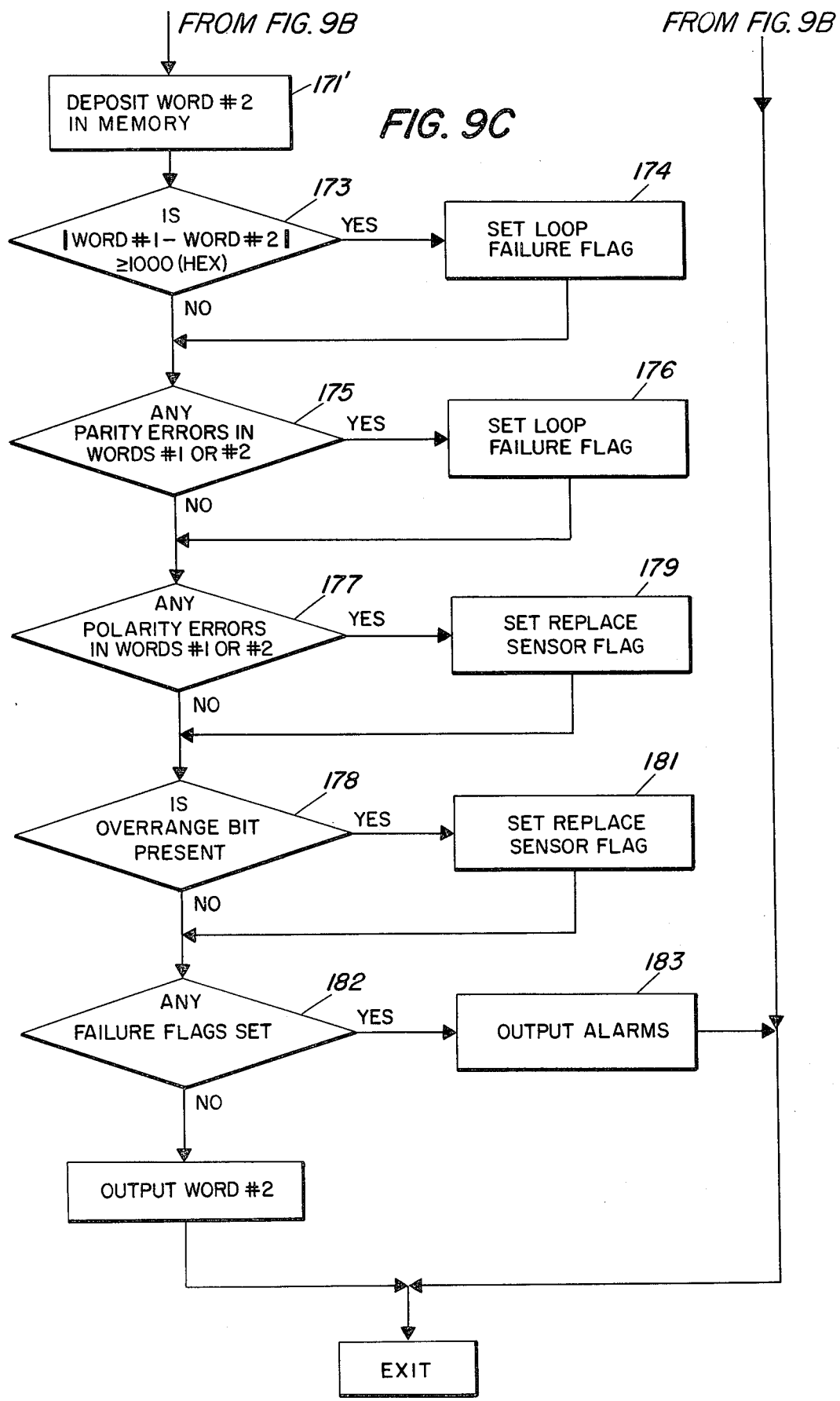

COMBUSTIBLE GAS DETECTION SYSTEM

The present invention relates to combustible gas detection systems. More particularly, it relates to a combustible gas detection system with sensors remotely located from a central control station and with digital data transmission and processing means.

In many large manufacturing operations, plant conditions are monitored from a central control station where data is received from remotely located sensors and processed for control or alarm purposes. For combustible gases, the sensors in widest use are of the catalytically activated type disclosed in U.S. Pat. No. 3,092,799 to A. R. Baker for "Apparatus for Detecting Combustible Gases Having an Electrically Conductive Member Enveloped in a Refractory Material". Such sensors provide a low level analog signal output indicative of the concentration of combustible gas to which the sensor is exposed. Sensors of this type must be calibrated prior to use and periodically thereafter to account for differences in sensitivity and aging effects. In conventional systems the sensor signal output, as seen at the control station, is affected by the characteristics of the transmission line connecting the sensor with the controller. Calibration requires the services of two operators, one located at the sensor to expose the sensor to test gases and the other located at the controller to perform the necessary adjustments. In such systems no means are provided to warn of faulty calibration procedures, to warn of aged and insensitive sensors or to warn of failures in the data processing loop. Prior systems, upon issuance of an alarm, give no indication of whether the alarm was the result of a fault in the system or whether the alarm was a valid warning of the existence of a dangerous concentration of combustible gas at the sensor location.

In U.S. patent application Ser. No. 315,684 filed Oct. 27, 1981 for Combustible Gas Detection System by J. K. Winner, now U.S. Pat. No. 4,422,073, there is disclosed a combustible gas detection system in which signals are digitally transmitted from a remote sensor to a controller thereby eliminating the effect of the transmission line in the signal. With such signal transmission means and with the data processing means of the present invention no manual adjustments need be made at the controller. The controller can perform an auto-calibration and the services a single operator are required only to expose the sensor to test gases. The controller also provides means for distinguishing system faults from valid alarm conditions and in the event of system fault vocally annunciates the nature of the malfunction.

It is an object of the present invention to provide a combustible gas detection system having means for auto-calibration of remotely located sensors.

It is another object of the invention to provide a combustible gas detection system having means for determining and indicating that sensor replacement is required because of declining sensitivity.

It is a further object of the invention to provide a combustible gas detection system in which accuracy of output data is increased by compensating for inherent non-linearity of the sensor.

Another object of the invention is to provide a combustible gas detection system which monitors against system faults and which is capable of identifying the nature and location of such faults.

Further objects and advantages of the invention will appear as a complete understanding thereof is gained through study of the accompanying complete description.

Briefly, the invention comprises remotely located combustible gas sensors which provide analog outputs indicative of the combustible gas concentrations at their locations. Means are provided for converting sensor analog data to digital data and for transmitting such digital data to a central controller. At the controller the data is variously tested to determine the integrity of the sensor data conversion and transmission means and is further tested for validity by comparison with expected ranges of sensor outputs. If the integrity and validity tests are passed, the controller computes the concentration of combustible gas at a sensor location, compares the value with predetermined alarm set points and generates alarms, if necessary. If any of the various data tests are failed, means are provided for vocally identifying the particular test or tests which have been failed.

In the drawings:

FIG. 1 is an elevation of the front panel of the controller of the invention;

FIG. 2 is a functional block diagram of the invention;

FIG. 3 is a flow chart of the main program of the controller microprocessor;

Figure 7A:
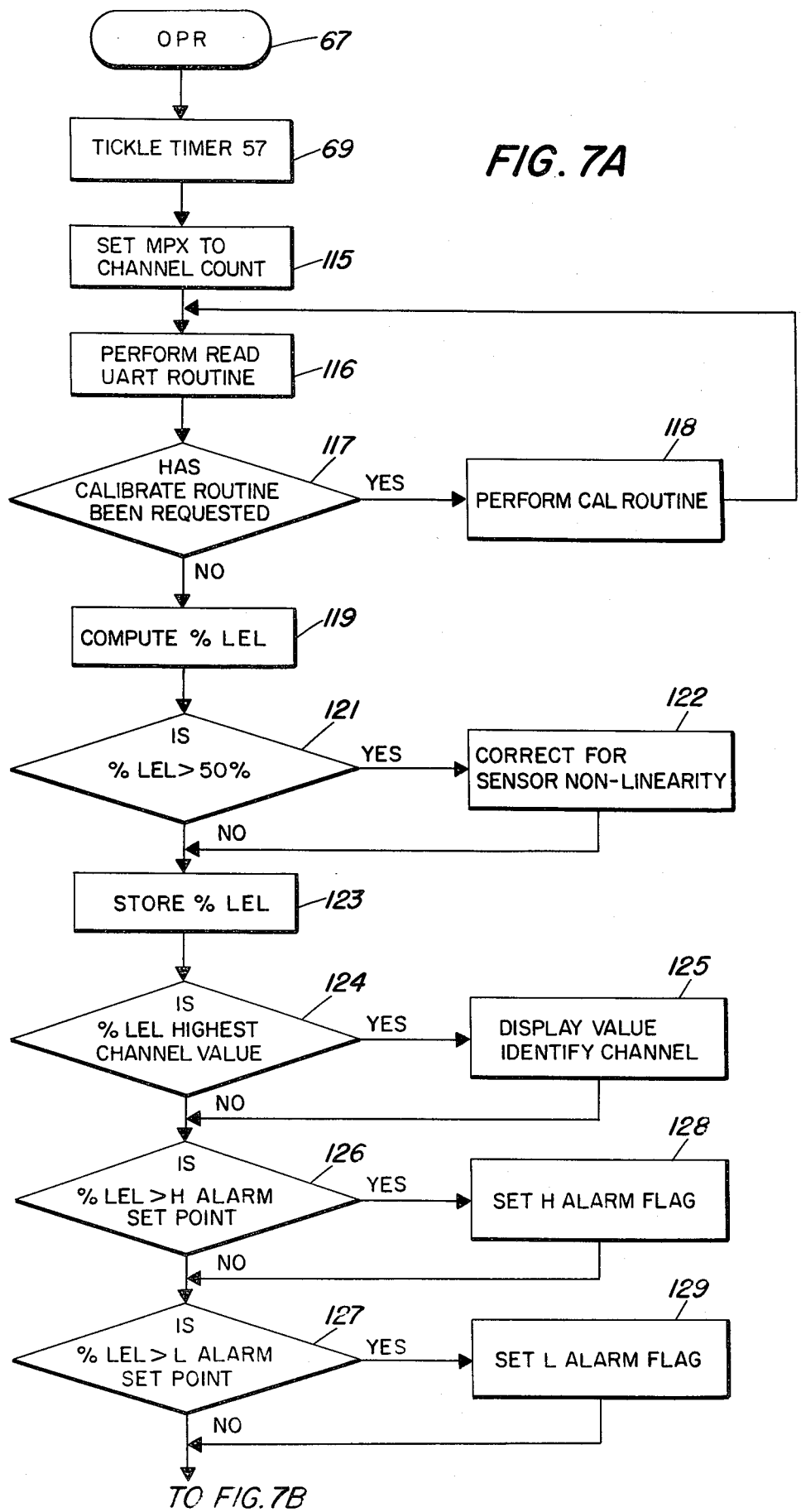
Figure 7B:
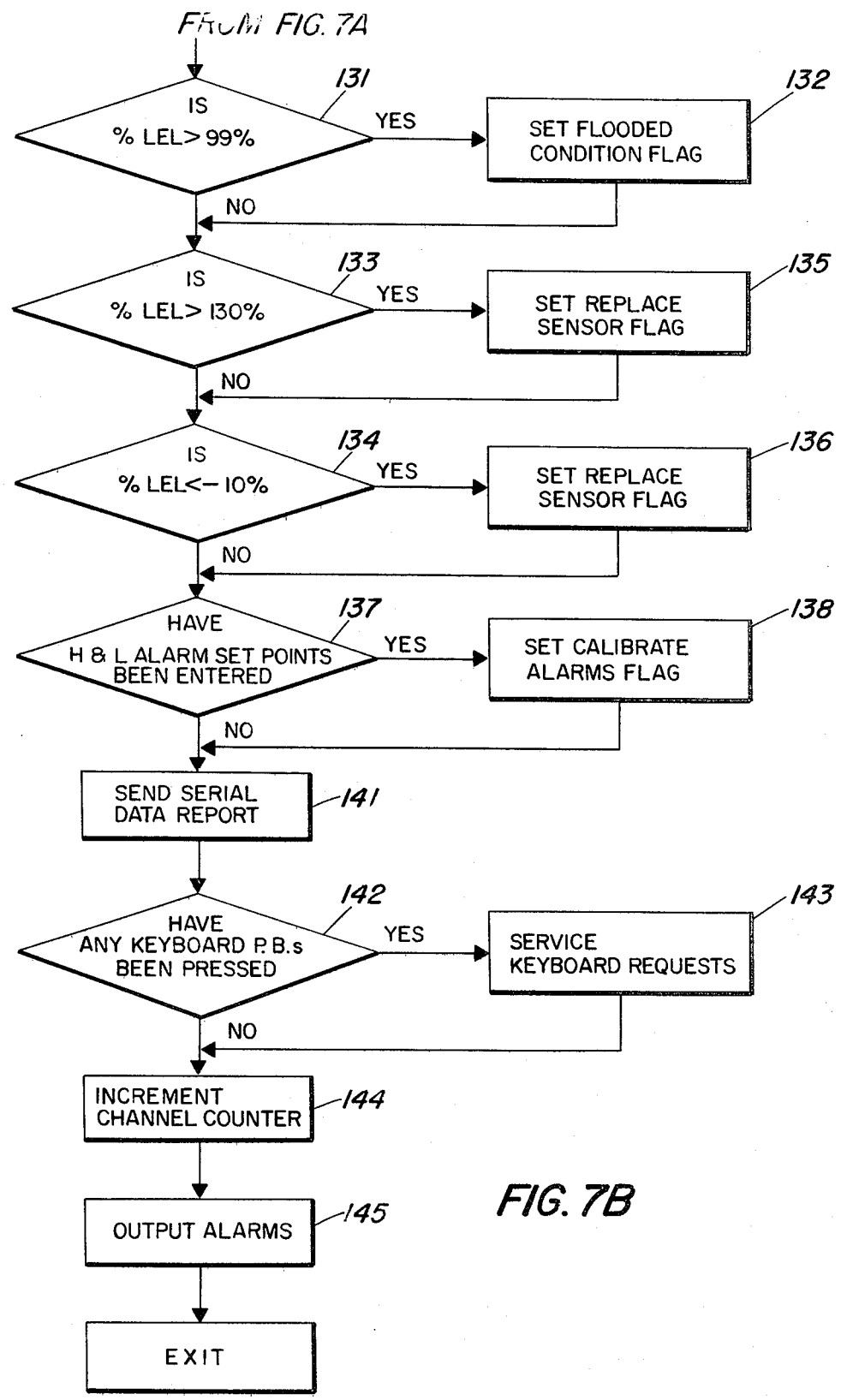
Figure 9B:
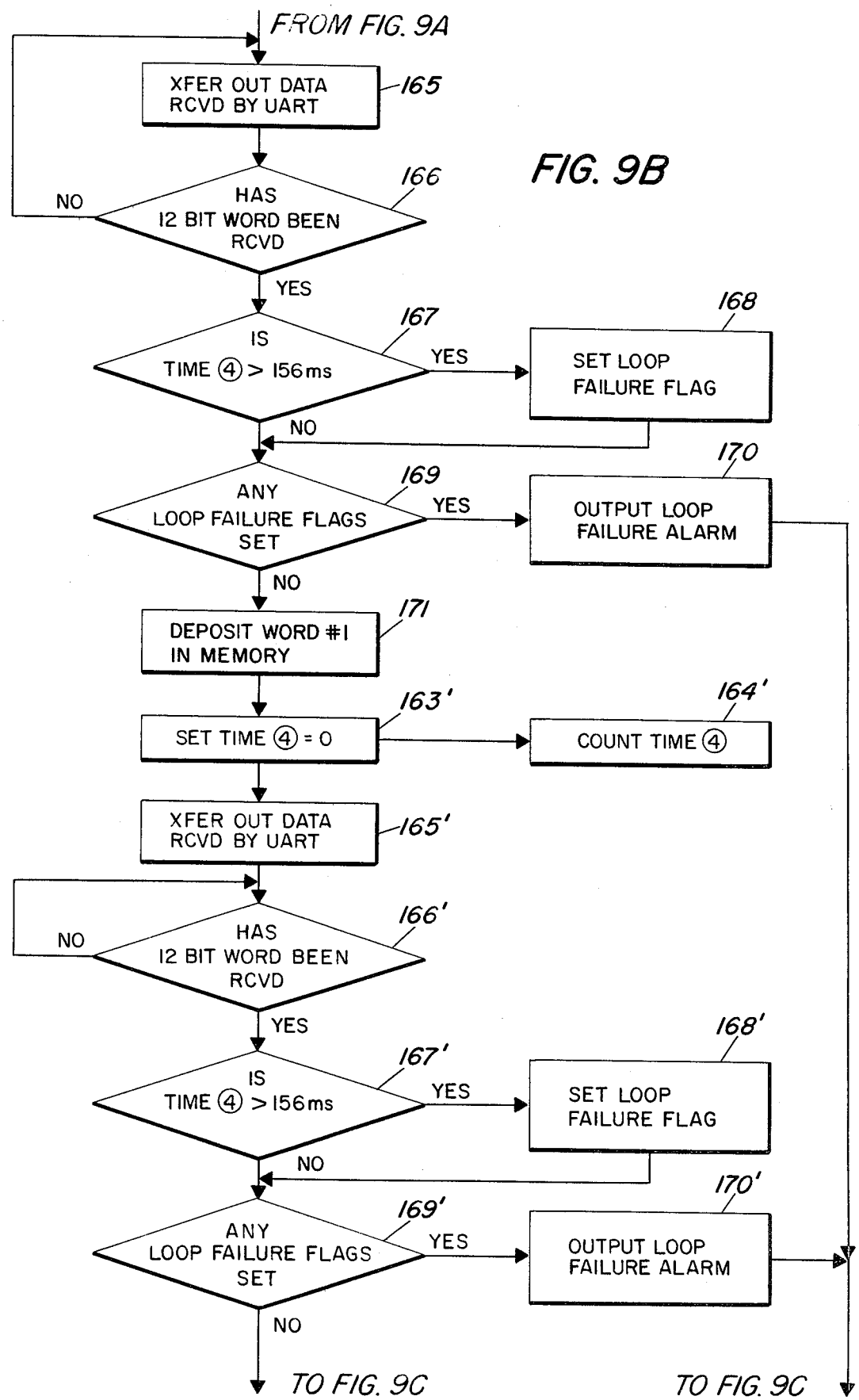
Figure 10A:
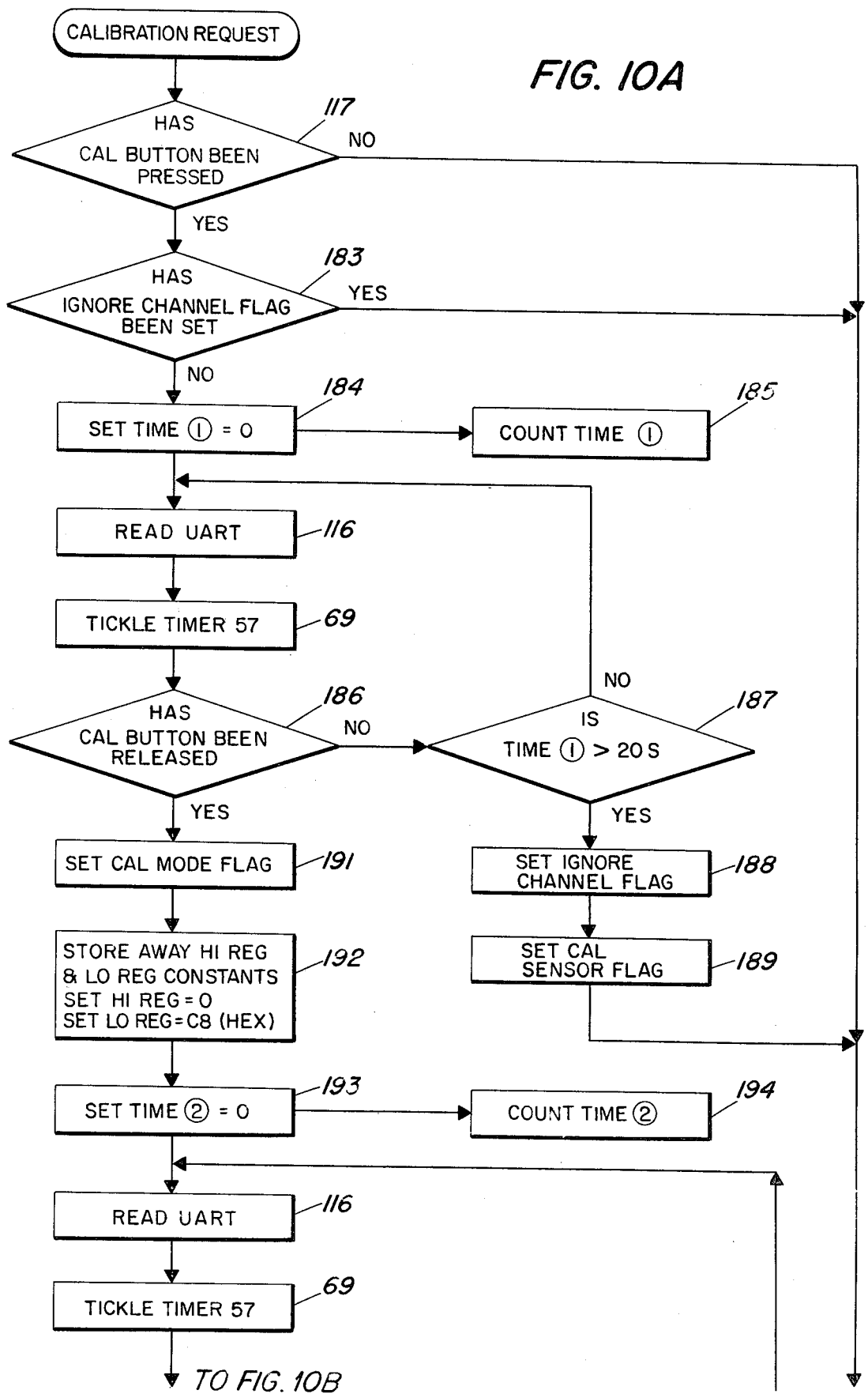
Figure 10B:
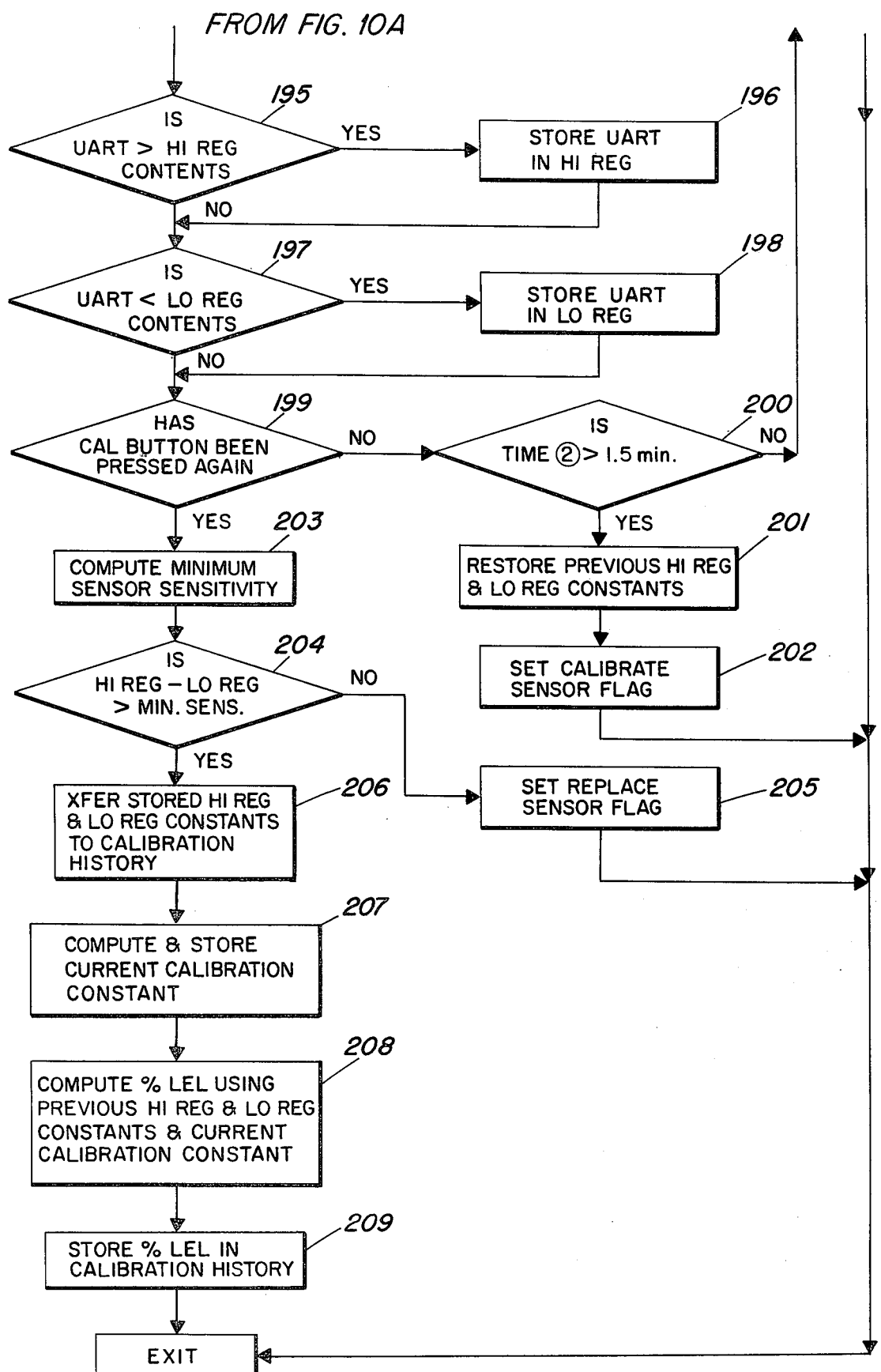

FIGS. 7A and 7B, assembled, is a flow chart of the OPR routine of the main program used in normal operation of the invention;

FIG. 8 is a diagram illustrating the data format used in the invention;

FIGS. 9A, 9B and 9C, assembled, is a flow chart of the READ UART subroutine used in the OPR routine to insure the validity of the data to be processed; and FIGS. 10A and 10B, assembled, is a flow chart of the CALIBRATION REQUEST subroutine used in the OPR routine to enable calibration of remotely located sensors by one person.

FIG. 1 is an illustration of the front panel of the controller of the invention. In the specific embodiment to be described provision is made for serving five remotely located combustible gas sensor modules, although obviously the invention is not limited to any particular number of sensor module channels. At the upper portion of the controller panel a numerical display 10 appears comprising two decimal digits formed by conventional seven segment LED indicators. A speaker, concealed by a protective grill 11, provides audible information in the form of vocal messages for identifying the nature of a malfunction in the system or tones for calling attention to system faults.

A 4×5 back-lighted keyboard matrix 12 is mounted beneath the speaker grill. The 4 keys of each row of the keyboard are labeled respectively with a channel number, H, L and F. The 5 rows of keys are associated with individual sensor channels.

A 4-position mode switch 13 is located below the keyboard 12. The positions of switch 13 are labeled respectively "CAL SET", "RST", "OPR" and "AL SET". When switch 13 is in the "CAL SET" position, keyboard 12 is connected for data input to the microprocessor and the indicator 10 displays the decimal value of the data being entered. "CAL SET" is used to enter into the controller microprocessor memory the value of the test gas in terms of percent lower explosive limit (LEL) of the test gas which will be used to calibrate each of the sensor modules. For instance, the LEL of methane is a concentration of 5% by volume in air. If a 2.5% concentration of methane is used as test gas, the specific data to be entered during "CAL SET" is 50. This is accomplished by depressing a channel number on keyboard 12 corresponding to the sensor at which that gas is to be used, then successively depressing the H button for that channel, causing indicator 10 and the data it represents to be incremented in steps of 1% until the desired value is reached. The L button for that channel causes the data to be decremented in 1% steps for each button depression, should it be necessary to reduce the value of the data.

In the "AL SET" mode, the keyboard 12 and display 10 provide means for entering and displaying the high and low set points of LEL desired for each channel. For instance, if it is desired that a low alarm be given when the gas concentration at a particular sensor reaches 25% LEL, the L button is successively depressed, causing the display and the data it represents to be incremented in 5% steps until the value 25 is displayed. Similarly, the high alarm set point is entered by successively depressing the H button until the value desired for the high alarm set point is reached.

The controller is placed in the normal operating mode when switch 13 is positioned at "OPR". In this mode the controller automatically selects the channel having the highest percentage LEL detected for any of the 5 sensor channels and displays the percentage value for that channel on indicator 10 and also identifies that channel by illuminating the corresponding channel button on keyboard 12. The operator may examine the percentage LEL of combustible gas present at any other sensor location by pressing any of the channel selector buttons on keyboard 12, whereupon the percentage LEL for that channel will be momentarily indicated on the display 10.

If the combustible gas concentration at any sensor location exceeds the low alarm set point, the L button for that channel will be illuminated with a flashing yellow light and an external alarm will be activated, if the system is so equipped. Similarly, if the combustible gas concentration at any sensor location exceeds the high alarm set point, the H button of keyboard 12 for that channel will be illuminated with a red flashing light and an external alarm, if provided, will be actuated. If a malfunction should occur in any sensor channel the F button of keyboard 12 for that channel is illuminated with an amber light.

When switch 13 is positioned at "RST" the controller is placed in the reset mode. Whenever the set point for the high or low alarm of any channel is exceeded the warning lamp and external alarm are latched in an active condition. Pressing the activated alarm button during reset unlatches the alarm and prepares the controller for normal operation upon return to the "OPR" mode, provided the condition which caused the alarm has dissipated. Pressing any lighted F button during reset causes a vocal pronouncement of the nature of the fault to be made through speaker 12. A description of the faults thus identified appears hereinafter.

FIG. 2 is a functional block diagram of the invention. In this specific embodiment, a controller 15 services up to five remotely located sensor modules 16. Each sensor module includes a catalytically active combustible gas sensor 17 which produces an analog output signal indicative of the concentration of combustible gas present at the sensor location. The analog output of sensor 17 is converted to a parallel format digital signal by a digital-to-analog converter 18. A universal asynchronous receiver transmitter (UART) 19 receives the parallel format digital signal from converter 18 and transforms it into serial format digital data for transmission by a frequency shift keying modulator 21 upon a transmission line 22 linking the sensor module 16 with the controller 15. The sensor module 16 and its associated data transmission means are more fully described in the above-referenced patent of Winner.

A microprocessor unit (MPU) 25 is at the center of controller 15. Storage of program instructions and other static data is provided by a read only memory (ROM) 26, while storage of dynamic data is provided by a random access memory (RAM) 27. Both memory units 26, 27 are controlled and accessed by the MPU 25 in a conventional manner. Entry of data into and delivery of data from MPU 25 is controlled by a programmable interface element (PIE) 28. Under command of MPU 25, PIE 28 controls the writing of data on data bus 29 through input ports 31 and 32 and the reading of data on the data bus by output devices through output ports 33–38. Input ports 31, 32 and output ports 33–38 each comprise a buffer register for the temporary storage of input-output data. Control of output ports 33–38 is effected by PIE 28 through a command decoder 39 which decodes address instructions on the data bus 29 to provide control signals A–F to individual output ports 33–38.

Data relating to the concentration in terms of percentage LEL of the test gas used for calibration is written into RAM 27 through keyboard encoder 41 and input port 31, mode switch 13, then being positioned at "CAL SET", identifies the nature of the data being entered. Similarly, data relating to high and low alarm set points enters through port 31, while mode switch 13, positioned at "AL SET", identifies the data being entered as alarm set points.

Data from the remote sensor module 16 relating to the concentration of combustible gas present at the sensor location enters the controller through an input multiplexer 42 which connects the transmission line from one of the five possible input channels to an FSK detector 43. Detector 43 converts data present on a transmission line in the form of two different tones, one representative of binary "0" and the other representative of binary "1", to direct voltage levels. The direct voltage serial digital data from detector 43 is received and stored by a UART 44 which, on command of PIE 28, transfers the stored data to data bus 29 in parallel digital format.

Input port 32 furnishes data to MPU 25 indicating the number of sensor channels in use, provided by a channel selector switch 45, and data indicating a malfunction in the system power supply, provided by a power supply monitor 46.

Output data from MPU 25 is transferred to peripheral devices through output ports 33–38. In the "OPR" mode MPU 25 determines the sensor channel at which the highest percentage LEL is present and transfers the value of such concentration through output port 34 and display decoder 47 for indication on the numerical display 10 while the channel being displayed is identified by data transferred through output port 35 to the channel indicator LEDs 48. Information on the percentage LEL concentration of combustible gas at the sensors for all other channels is present in RAM 27 and these may be called up for display by pressing the channel button of keyboard 12 for the desired channel. If the combustible gas concentration should exceed the high or low alarm set points, alarm signals are transferred through output port 38, flasher register 49, and logic 51, which is interconnected with the LED drivers 48, to flash the appropriate one of the LEDs illuminating the H and L buttons of keyboard 12. Simultaneously an audible external alarm 52 is energized by an alarm signal passing through output port 37 to latch alarm relay drivers 53. Should the MPU 25 detect a system malfunction or a malfunction in the sensor for any channel, an alert signal is transferred through output port 38 and flasher register 49 to illuminate the appropriate F button of keyboard 12 identifying the faulty channel. A permanent record of gas concentrations detected at all channel sensors may be provided with data transferred through output port 36 and a D/A converter 54 to a chart recorder 55. If the MPU 25 has detected a malfunction for any sensor channel, data is transferred through output port 33 to conditionally enable pronunciation of one or more of nine phrases stored in a voice synthesizer 56. Upon depressing the illuminated F button of keyboard 12 when mode switch 13 is in the RST position, the enabled phrase or phrases of voice synthesizer 56 are vocalized through speaker 11 to identify the nature of the malfunction. The phrases stored by synthesizer 56 are as follows.

"Sensor failure" is pronounced if an electrical fault is present in the catalytic sensor but the sensor electronics, sensor transmission line and controller are otherwise functioning properly.

"Calibrate sensor" is pronounced if the calibration procedure has not been followed properly, including failure to enter the test gas concentration when the controller is in the CAL SET mode, or if such data has been lost from memory due to power failure.

"Replace sensor" is pronounced if the sensitivity of the catalytic sensor has fallen below a tolerable level due to aging, poisoning or other defect or if some error has been committed during calibration procedure, such as use of a test gas having a concentration other than the test gas concentration entered during CAL SET.

"Loop failure" is pronounced whenever improper or defective data is received from a sensor channel.

"Power failure" is pronounced on loss of operating or back-up power.

"Calibrate alarms" is pronounced if high and low alarm set points have not been entered for each channel in use or if such data has been lost because of power failure.

"Calibrate mode" is pronounced to indicate that a calibration procedure is being performed on a sensor.

"Flooded condition" is pronounced whenever a catalytic sensor has been exposed to a gas concentration in excess of 99% LEL. Such concentrations saturate the sensor and render data therefrom unreliable for a substantial period of time following the over exposure.

"Mode failure" is pronounced whenever the channel selector switch 45 is not set correctly to correspond to the number of channels in use.

A further indication of controller failure is provided in the form of a warbling tone triggered by a software failure timer 57, should the microprocessor 25 fail to continuously complete program routines within a prescribed time.

MPU 25 is programmed in accordance with the instructions set-out in FIGS. 3–7, 9 and 10. Referring to FIG. 3, the main program, the initial instruction 62 is to check the position of mode switch 13. Next, at 63 the MPU is instructed to perform the routine specified by the position of mode switch 13 which may be AL SET 64 for the purpose of entering H and L alarm set points; CAL SET 65 for the purpose of entering constants relating to the span gas to be used during calibration of the sensor module 16; RST 66 for resetting alarms which may have been triggered by a system fault or by a dangerous concentration of combustible gas and OPR 67 during which the system performs its normal task of monitoring the remotely located sensor modules and warning of the existence of dangerous conditions at any such location.

Upon exiting from any of the routines 64–67 an update instruction 68 is issued which will enable transfer of data from output port 36 through D/A converter 54 to chart recorder 55. Thereafter, instruction 69 is given to tickle software failure timer 57 and then return to instruction 62 for program repeat.

Software failure timer 57 is comprised by a retriggerable multivibrator having a time constant of approximately 10 seconds. A "tickle timer 57" instruction to the MPU causes a trigger to be applied to timer 57 which sets the output thereof high for approximately 10 seconds. So long as tickle instructions are received by the MPU at intervals of less than 10 seconds, the output of timer 57 will remain high and no software failure alarm will be generated.

Figure 4:
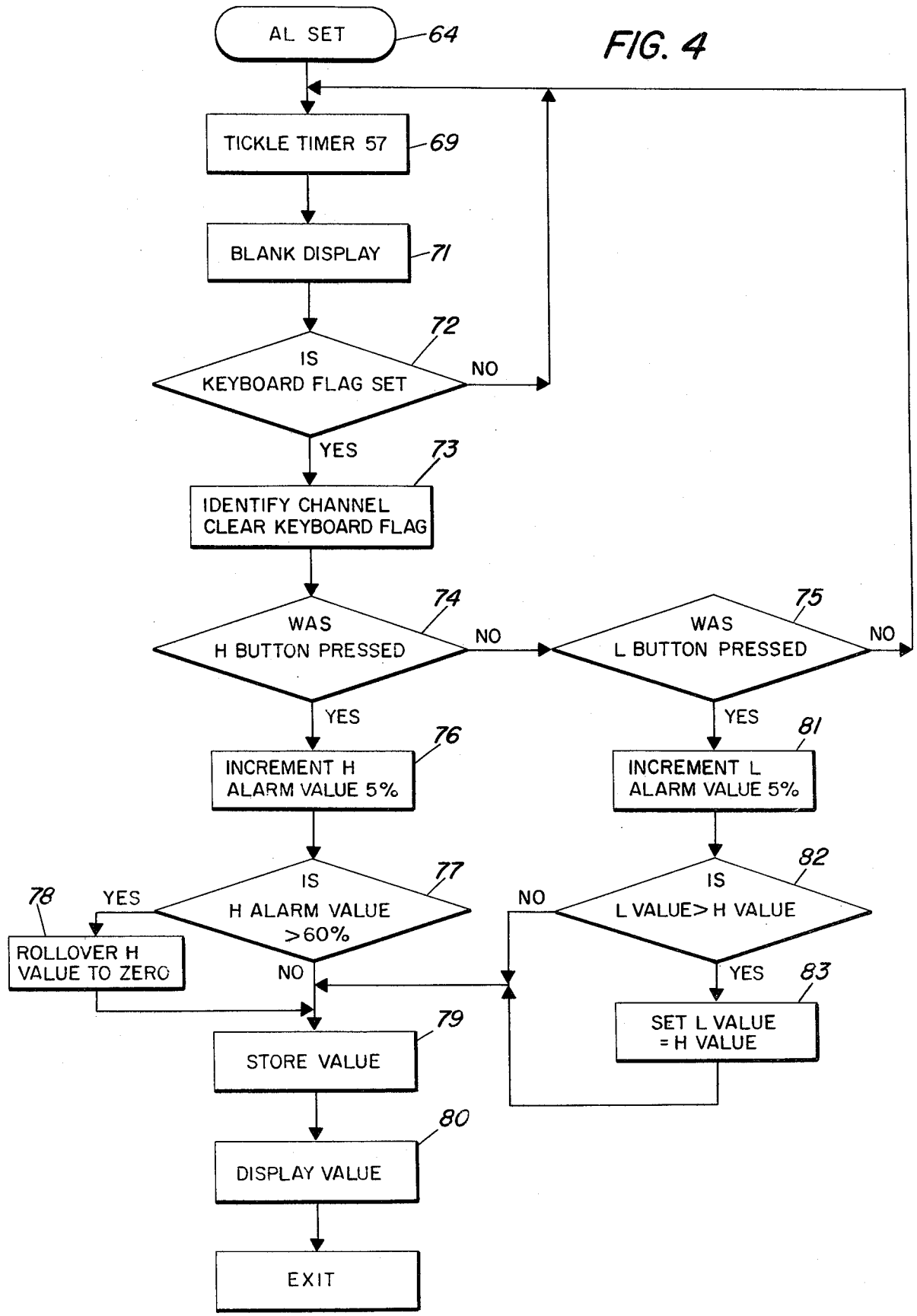
FIG. 4 is a flow chart of the AL SET routine of the main program used for entering alarm set points into the microprocessor.

The AL SET routine 64 is shown in FIG. 4. The purpose of AL SET is to enable the system operator to enter high and low alarm set points for each of the channels being monitored. For instance, the operator may wish to be alerted to a gas concentration of 25% LEL at a particular location so that early measures might be taken to control a potentially dangerous situation and he may wish to know when the concentration has further increased to say 50% LEL, so that emergency control measures may be taken. Accordingly, the L alarm would be set to 25% and the H alarm would be set to 50%.

Upon entering this routine instruction 69 is given to retrigger timer 57, then any data being indicated by display 10 is erased with blank display 71 and keyboard encoder 41 is tested by instruction 72 to determine whether a flag has been set indicating that one of the buttons of keyboard 12 has been pressed. If not, the program loops back to the entry point and continues to circulate through instructions 69, 71 and 72 until a keyboard button has been pressed. Upon detecting the closure of a keyboard button the channel with which the closed button is associated is identified and the keyboard flag is cleared at 73. Next the closed button is identified as an H button at 74 or as an L button at 75. If the closed button was neither for H nor L, as might occur if the operator mistakenly presses a channel number or an F button, the program returns to the starting point. If test 74 determines that an H button was pressed, instruction 76 is given to increment the H alarm set point for the identified channel an amount of 5%. The new alarm set point is then tested at 77 to determine whether the value is greater than 60% LEL. If so, instruction 78 causes the H alarm set point to be rolled over to zero, thereby preventing any H alarm being set to a value greater than 60% LEL. Then at 79 either the selected H alarm set point less than 60% LEL or zero percent LEL is stored for the identified channel, indicated 80 on display 10 and the routine is exited.

If test 75 determines that the button pressed was for L, instruction 81 is given to increment the L alarm set point stored for the identified channel an amount of 5%. The new L alarm set point is then tested at 82 to determine whether its value is greater than the H alarm set point for the identified channel. If so, instruction 83 is given to replace the L alarm set point with the value of the H alarm set point, thereby preventing any L alarm from being set to a higher value than the H alarm set point. After acceptance of the L alarm set point in test 82 or its replacement by instruction 83, the value is stored, displayed and the routine is exited.

Figure 5:
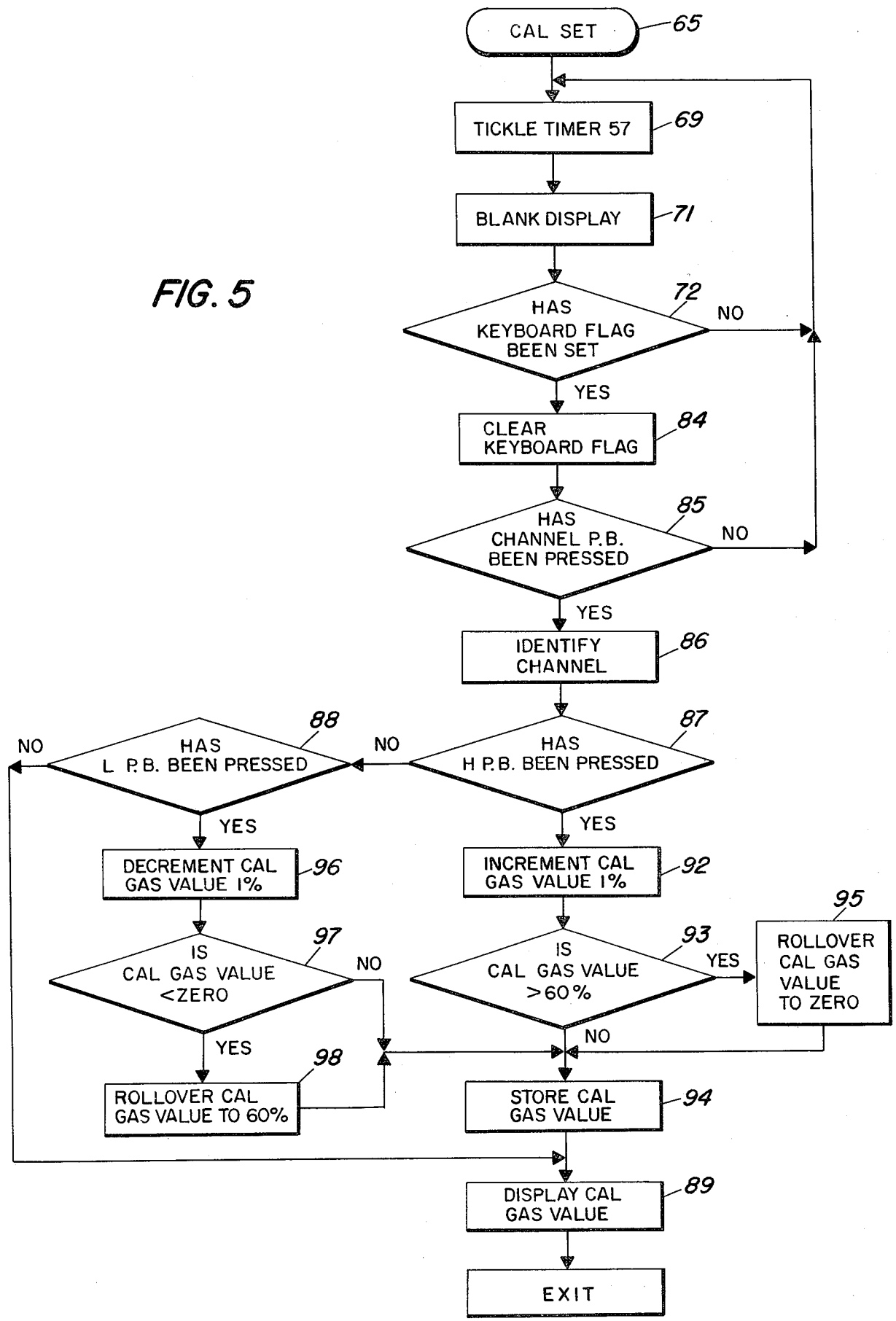
FIG. 5 is a flow chart of the CAL SET routine of the main program used for entering calibration gas constants into the microprocessor.

The CAL SET routine is shown in the flow chart of FIG. 5. The purpose of CAL SET is to enable the system operator to enter into MPU 25, the percent LEL of the span gas to be used in the calibration of the sensor modules 16. Upon entering this routine, instruction 69 is given to apply a trigger to timer 57, display 10 is blanked and keyboard 41 is tested for the presence of a flag indicating that one of the buttons of keyboard 12 had been pressed. If no keyboard buttons have been pressed the program loops through instructions 69, 71 and 72 until a keyboard encoder flag is detected. Then the keyboard flag is cleared 84 and the encoder is tested 85 to determine whether a channel number pushbutton has been pressed. If no channel number has been pressed the program loops back to start and continues to circulate through 69, 71, 72, 84 and 85 until the operator identifies a channel, by pressing a channel number button, to which the data to be entered applies. After a channel button has been pressed the channel is identified and the encoder is tested 87 for closure of an H pushbutton. If an H button has not been pressed test 88 is made for closure of an L button. If neither an H nor an L button has been pressed the program jumps to instruction 89 causing the percent LEL value of the calibration gas previously entered for the identified channel to be displayed and the routine is exited.

If test 87 determines that an H pushbutton has been pressed, instruction 92 is given to increment the calibration gas percent LEL stored for the identified channel by 1%. Test 93 is made to determine whether the new calibration gas percent LEL exceeds 60%. If not, instruction 94 is given to store the new calibration gas percent LEL for the identified channel, display that value and exit. If test 93 shows that a calibration gas value greater than 60% LEL has been entered, instruction 95 is given to roll-over to zero the calibration gas value for the identified channel, store the same, display it and exit.

If test 88 determines that an L pushbutton has been pressed, instruction 96 is given to decrement by 1% the calibration gas percent LEL stored for the identified channel, following which the new calibration gas value is tested determine whether a value less than zero has been entered. If not, the new calibration gas value is stored for the identified channel, displayed and the routine is exited. If test 97 determines that a calibration gas value less than zero has been entered, instruction 98 is given to roll-over the value to 60% whereafter the 60% value is stored for the identified channel, displayed and the routine is exited.

The operating procedure for entering calibration gas constants into MPU 25 therefore involves setting mode switch 13 to CAL SET and pressing a channel number pushbutton, causing the calibration gas percent LEL previously entered for the identified channel to be displayed. If the previously entered calibration gas constant conforms to that of the span gas to be used for the selected channel sensor, no further action need be taken. If adjustment is required, the previous calibration gas value is incremented or decremented the necessary amount by successively pressing an H or L button.

Figure 6:
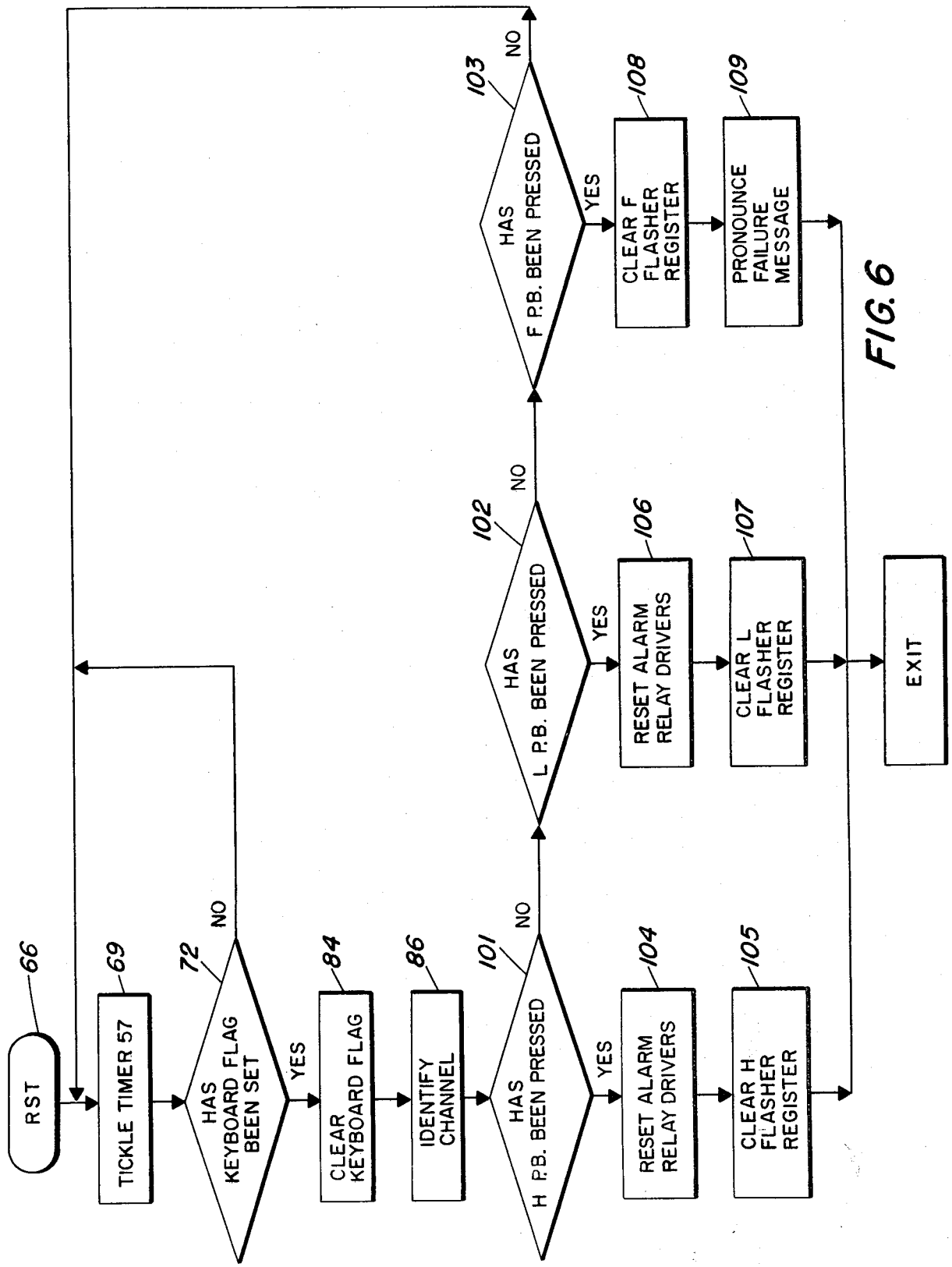
FIG. 6 is a flow chart of the RST routine used for resetting any alarms latched during operation of the invention.

The flow chart for the RST routine 66 appears in FIG. 6. The purpose of this routine is to enable reset of any alarms which may have been tripped and latched by the presence of a gas concentration at any of the sensors in excess of the H or L alarm set points and to enable the vocal pronouncement by voice synthesizer 56 of any failure messages enabled by the existence of a system fault.

Upon entering RST instruction 69 is given to retrigger timer 57. Then test 72 is made to determine whether a flag had been set in encoder 41 indicating that one of the buttons of keyboard 12 had been pressed. If not, the routine loops through instruction 69 and test 72 until closure of a keyboard button is detected. Then the keyboard flag is cleared 84 and the channel associated with the pressed button is identified 86. Next, tests 101, 102 and 103 are applied to detect whether the button closed was an H, L or F button. If test 101 for an H button is positive, instruction 104 is given to reset any latched H alarm relay driver 53 and 105 clears the H portion of flasher register 49. Then the routine is exited. If test 102 is positive, instruction 106 resets latched L alarm relay drivers and 107 clears the L portion of flasher register 49. Then the routine is exited.

If test 103 is positive, instruction 108 clears the F portion of flasher register 49 and instruction 109 enables voice synthesizer 56 to pronounce the appropriate failure message. Then the routine is exited.

FIGS. 7A and 7B, assembled, is a flow chart of the OPR routine 67. FIG. 8 illustrates the format of serial data transmitted by UART 19 of sensor 16 (FIG. 2). Referring to FIG. 8, a complete sensor data word comprises two bytes 111, 112 of 12 bits each and a third byte 113 of 18 bits length in which no transitions from the logic "1" level occur. A/D converter 18 of sensor module 16 is capable of resolving the analog input voltage from sensor 17 into 12 data bits, while UART 19 is capable of transmitting a data word of only 8 bits length. It is therefore necessary to break the data output of A/D converter 18 into 2 bytes 111, 112. Byte 111 contains the high order bits $B_9$–$B_{12}$ of the data output of converter 18 with bit $B_{12}$ being the most significant bit. Byte 112 contains the lower order bits $B_1$–$B_8$ of converter 18 data with bit $B_1$ being the least significant bit. The first bit of bytes 111 and 112 is always at logic "0" level and is used for the purpose of synchronizing the receiving UART 44 of controller 15 with the transmitting UART 19 of sensor module 16. Bits 11 and 12 of bytes 111 and 112 are always at logic "1" level, signalling the end of each byte. The second bit of byte 111 is reserved to signal a calibration request from sensor module 16 to controller 15. If this bit is set to logic "1" by closure of calibrate switch 20 at sensor module 16, MPU 25 enters the CALIBRATION REQUEST subroutine, as will later be described. The third bit of byte 111 is not used; the fourth through seventh bits are data bits $B_9$–$B_{12}$; the eighth bit, if logic "1", indicates that the analog input to converter 18 is greater than the converter range; the ninth bit, if logic "1" indicates that the analog input to converter 18 is of positive polarity and the tenth bit shows the parity of bits $B_9$–$B_{12}$. In byte 112 the second through ninth bits are data bits $B_1$–$B_8$ and the tenth bit indicates the data bit parity. Data from UART 19 is transmitted at the rate of 300 bits per second. Bytes 111 and 112 therefore occupy a period of approximately 40 ms. while the period of byte 113 is approximately 60 ms.

Referring to FIGS. 7A and 7B, assembled, at the beginning of the OPR routine 67 instruction 69 is given to tickle timer 57, then instruction 115 is given to set input multiplexer 42 to the count contained by the channel counter of MPU 25. The channel counter cycles between 1 and the number 5 or less set on channel select switch 45 indicating the number of channels in use. After selecting an input channel, instruction 116 is given to perform the READ UART routine, later to be described. After completing READ UART a valid data word is available which includes the 12 bit digital equivalent of the millivolt analog output of combustible gas sensor 17. The format of this word has been described with reference to FIG. 8. The first byte 111 is tested 117 for the presence of logic "1" in the first bit position. If "1" is present at this position, a calibration routine 118, later to be described, has been requested and that routine is immediately performed. Upon exiting from the calibration routine, READ UART is again performed and, assuming that calibration has not again been requested, the percentage LEL is computed 119 using the 12 bit data word in the following formula:

$$\% LEL = \frac{V - V_o}{C} \quad (1)$$

where:
V = current sensor reading, mv.
$V_o$ = stored sensor reading for zero gas
C = calibration constant, mv./% LEL.

The constants $V_o$ and C are obtained and stored during the calibration routine. Test 121 determines whether the computed percent LEL exceeds 50%. If so, the sensor is operating in a nonlinear response region so that reference is made to a look-up table 122 for corrected data output. Below the value of 50% the sensor data may be used without correction. Either the non-corrected or corrected percent LEL is stored 123 at a memory location reserved for the particular channel being examined. That value is then checked 124 against similar values previously stored for all other channels in use to determine the channel having the highest percent LEL. If the channel being examined is the highest, instruction 125 is given to display the value and to identify the channel by illuminating the channel number pushbutton. The percent LEL is then tested 126 against the high alarm set point and tested 127 against the low alarm set point. If the percent LEL exceeds either of these set points either or both H alarm flag and L alarm flag are set by instructions 128, 129. Test 131 determines whether the percent LEL exceeds 99%, in which case the flooded condition flag is set 132. Tests 133 and 134 determine whether the percent LEL is greater than 130% or less than −10%. If either of these tests is failed, the replace sensor flag is set by instruction 135 or 136.

Test 137 is conducted to determine whether H and L alarm set points have been entered for the particular channel during the AL SET routine. If set points have not been entered for both H and L, the calibrate alarms flag is set 138. Instruction 141 is then given enabling UART 44 to transmit its current contents through serial data output port 142 (FIG. 2) to a central data processor where it may be used for control or record purposes. Keyboard encoder 41 is checked for the entry of any requests, such as display of percent LEL for a particular channel, and such requests are serviced 142, 143; the channel counter is incremented 144 so that the next time the routine is performed it will apply to the channel next in order and finally, any alarms called for by a set alarm flag are generated 145 and the routine is exited.

The flow chart for READ UART routine appears in FIGS. 9A, 9B and 9C, assembled. Upon entering the routine instruction 69 is given to retrigger timer 57. Then the first two words received by UART 44 are disregarded, so far as their information content is concerned, but are checked for tolerable conformance to the word period of approximately 160 ms. by the following means. Referring briefly to FIGS. 2 and 8, retriggerable multivibrator 58 receives a trigger input from the serial data output of detector 43. Multivibrator 58 is triggered by a low to high transition in the data output of detector 43 and after triggering the multivibrator output remains high for a period of 50 ms. The output of MV 58 is available for examination by MPU 25 through input port 32. In the data format of FIG. 8, if all data bits of byte 111 were zero the longest time after the start bit before a trigger input to MV 58 appears is at the first stop bit, approximately 30 ms. after the end of the start bit. In byte 112 the latest possible time at which trigger will be applied to MV 58 is at the beginning of the first stop pulse and thereafter through the remainder of the word, including byte 113, no further trigger will be applied to MV 58. Therefore, if no fault exists in formatting or transmitting the data MV 58 should be low for approximately 15 ms. preceding the appearance of the start bit of byte 111 and the output of MV 58 may be high for as long as approximately 130 ms. An output transition of MV 58 should occur but once during each complete word.

Returning to FIG. 9, after retriggering timer 57, an internal timer of MPU 25 is started 147 and the output of MV 58 is tested 148 for low. If the output of MV 58 is not low the routine has been entered somewhere medially of a data word so the time set by instruction 147 is is simply counted 149, 150 until a transition in the output of MV 58 occurs. If such a transition does not occur within 182 ms. a loop failure flag is set 151. If an output transition of MV 58 does occur within the allotted time the internal timer of MPU 25 is reset 152 to zero and the time required for MV 58 to transition high is measured 153, 154, 155, 156. If MV 58 transitions high within 182 ms., the timer of MPU 25 is reset to zero 157 and the time required for MV 58 to transition low is measured 158, 159, 161. If such a transition does not occur within 182 ms., the loop failure flag is set 162. If a transition does occur within the allotted time the timer of MPU 25 is reset 163 to zero and now the data received by UART 44 is read-out 165. If the time set by instruction 163 does not exceed 156 ms. upon receiving a complete 12 bit word, the data is considered reliable and is deposited in memory as word #1, after first checking for the presence of any loop failure alarm flags 163–171. If any loop failure flags are detected at 169, the loop failure alarm is immediately given 170 and the routine is exited. If word #1 is acceptable, steps 163–171 (shown as 163′–171′) are repeated to deposit word #2 in memory. Then the absolute value of the difference between word #1 and #2 is checked 173 against the value 1000 (HEX) which is one-fourth the total dynamic range of 12 bit A/D converter 18. If that difference exceeds one-quarter of the total possible converter range, the loop failure flag is set 174. In a normally operating system a sensor cannot respond to changes in gas concentration occurring within the time span represented by word #1 and word #2 even if those changes were actually to occur at such rate.

If the dynamic range test 173 is passed, the parity bits of bytes 111, 112 are checked 175 for discrepancies with the data and if any exist the loop failure flag is set 176. The polarity and overrange bits of byte 111 are checked 177, 178 and if either is present, the replace sensor flag is set 179, 181. Finally, all failure flags are checked 182 and any indicated alarms are given 183, then the routine is exited; or word #2 is output as valid data, then the routine is exited.

The flow chart for the CALIBRATION REQUEST routine 118 appears in FIGS. 10A and 10B. As previously described, the present invention permits calibration of sensors remotely located from the central controller by one person who requires no assistance at the controller. The calibration procedure is initiated by closure of calibrate switch 20, whereafter the combustible gas sensor 17 is covered with a cup containing a flow of calibration (span) gas. The sensor 17 is exposed to calibration gas a sufficient time, say 20 seconds, to insure equilibrium conditions then the calibration gas is removed. The sensor is then exposed to clean air or, by means of a cup, to zero gas in which no combustibles are present, again for approximately 20 seconds to insure equilibrium, then calibrate switch 20 is again closed to signal the end of the calibration procedure.

Referring to FIGS. 10a and 10b, during the OPR routine 67 the output word produced during READ UART is tested 117 for the presence of logic "1" in the first bit position of byte 111. The closure of switch 20 introduces such a bit in the data word to cause MPU 25 to perform CALIBRATION REQUEST. Before entering the routine an ignore channel flag is tested 183 to determine whether a preexisting fault had caused the channel to be taken out of service. If such a flag is present the routine is immediately exited. If no such flag is present a timer is started 184, 185 and the READ UART routine 116 is performed. So long as the calibration switch 20 has not been released READ UART is continuously performed for a maximum of 20 seconds 116, 69, 186, 187. When calibrate switch 20 remains closed for longer than 20 seconds it is assumed that the button has become stuck. Then the ignore channel flag is set 188, the calibrate sensor flag is set 189 and the routine is exited.

When calibrate switch 20 is released within the allotted time the calibrate mode flag is set and the constants obtained during a previous calibration, if any, contained in a Hi register and a Lo register are temporarily stored away, while the Hi register is set to zero and the Lo register is set to an arbitrarily high number, C8 (HEX), 192. The purpose of setting the registers in this manner is to enable a maximizing process to be carried out. During calibration the sensor 17 analog output will initially be at a low level, not necessarily zero, then the output rises to a peak value corresponding to the concentration of the calibration gas and then falls off to a low level corresponding to zero gas. The maximum sensor output is to be stored in the Hi register and the minimum sensor output is to be stored in the Lo register.

After setting the registers to the initial condition the timer is restarted 193 at zero and READ UART is performed either until the end of calibration has been signalled or until 1.5 minutes have elapsed. As each data word is produced it is compared 195 with the current contents of the Hi register. If greater, the data replaces the contents 196. The same data is compared 197 with the current Lo register contents. If less than the Lo register contents, the data replaces the contents, 198. Thus, at the conclusion 199 of the calibration process, signalled by re-pressing calibrate switch 20, the Hi register will contain the digital equivalent of the highest millivolt output of sensor 17, corresponding to the concentration of the calibration gas and the Lo register will contain the digital equivalent of the lowest millivolt output of sensor 17, corresponding to zero gas.

If more than 1.5 minutes elapse before the end of calibration is signalled, the constants from the previous calibration, stored in step 192, are restored 201 to the Hi and Lo registers, the calibrate sensor flag is set 202 and the program is exited. If the calibration procedure is completed within the allotted time, the minimum sensor sensitivity is computed 203 by multiplying the calibration gas percent LEL by the factor 0.487. Thus, if a 50% LEL calibration gas is used the minimum sensor sensitivity is 24.35 mv. The digital equivalents of such numbers are, of course, used in the computation. If the difference between the Hi register and Lo register contents is not greater than such a minimum sensitivity 204, the replace sensor flag is set 205 and the routine is exited. If the difference between the Hi and Lo register contents exceeds the minimum sensor sensitivity the constants stored in step 192 are transferred 206 to a section of memory dedicated to calibration history.

The current calibration constant C, is computed 207 by dividing the difference between the Hi register contents and the Lo register contents by the percent LEL of the calibration gas. The Hi register and Lo register constants stored in step 192 are used with the current calibration constant to compute the percent LEL of the calibration gas 208, the results are stored in calibration history 209 and the routine is exited. The information stored in steps 206 and 209 is useful in tracing aging effects upon the sensor.

The invention claimed is:

1. A combustible gas detection system comprising, a sensor module located at a site to be monitored for combustible gas, said sensor module including, a combustible gas sensor providing an analog signal related to the concentration of combustible gas to which it is exposed;

means for converting said analog signal to a digital signal representing the numerical value of said analog signal, and means for transmitting said digital signal as a digital word having a predetermined serial data format; and a controller remotely located from said sensor module, said controller including, means for receiving said digital word transmitted by said sensor module;

means for testing the time duration of said received digital word to determine whether said time duration acceptably conforms to the time duration of said predetermined serial data format;

means providing the difference in value between two said digital words successively received;

means for testing said difference against a fixed value representing the maximum acceptable change between two said successive words;

means operable upon failure of said received words to meet said time duration test or said value difference test for providing a failure warning identifying data fault as the cause of failure;

computing means including a memory wherein calibration constants are stored, said calibration constants having been determined by exposure of said combustible gas sensor to gases of known concentrations of combustibles;

means applying said received word to said computing means for calculation from said received word and said stored calibration constants of the concentration of combustible gas present at said sensor module;

means for testing said calculated concentration against a predetermined range of probable values for such concentrations obtainable from a normal combustible gas sensor;

means operable when said calculated concentration is outside said predetermined range of probable values for providing a failure warning identifying said combustible gas sensor as the cause of failure;

means for comparing said calculated concentration with a predetermined alarm set point;

means providing an alarm signal whenever said calculated concentration exceeds said alarm set point; and means for displaying said calculated concentration of combustible gas.

2. A combustible gas detection system as claimed in claim 1 wherein said sensor module includes, additionally, means for modifying said digital word transmitted by said sensor module to signal the start and the finish of a calibration procedure wherein said combustible gas sensor is exposed to gases having a known concentration of combustibles; and wherein said controller includes, additionally, means responsive to the first said modified word received from said sensor module for causing said computing means to alter the mode of operation thereof to determine calibration constants from digital words received following receipt of the first said modified word, and means responsive to the second said modified digital word received from said sensor module for causing said computing means to return to the operation of calculating concentration of combustible gas from received words and stored calibration constants.

3. A combustible gas detection system as claimed in claim 2 wherein said computing means includes, means operative during said determination of calibration constants for storing the highest value digital word received and the lowest value digital word received, said highest value and lowest value words comprising calibration constants.

4. A combustible gas detection system as claimed in claim 3 wherein said controller includes, additionally, means for determining the difference between said highest value word and said lowest value word comprising calibration constants;

means for comparing said difference with a predetermined minimum value for said difference; and means providing a failure warning identifying said combustible gas sensor as the cause of fault whenever said difference is less than said predetermined minimum difference.

5. A combustible gas detection system as claimed in claim 1 wherein said controller includes, additionally, means for determining the presence of said predetermined alarm set point at said means comparing said calculated concentration with said alarm set point; and means operative in the absence of said alarm set point for providing a failure warning identifying the absence of said alarm set point as the cause of failure.

6. A combustible gas detection system as claimed in claim 5 wherein said controller includes, additionally, means for testing the value of said calculated concentration to determine whether said value exceeds the level of concentration of combustible gas at which said combustible gas sensor becomes saturated; and means operative whenever said calculated concentration exceeds said saturation level for providing a failure warning identifying saturation of said sensor as the cause of failure.

7. A combustible gas detection system as claimed in claim 6 wherein said controller includes, additionally, a voice synthesizer;

means for storing a plurality of failure messages differentiating sources of failure; and means controlled by all said failure warning means for selecting one said stored failure message and for enabling pronunciation of said selected message by said voice synthesizer.

* * * * *